Figure 1:
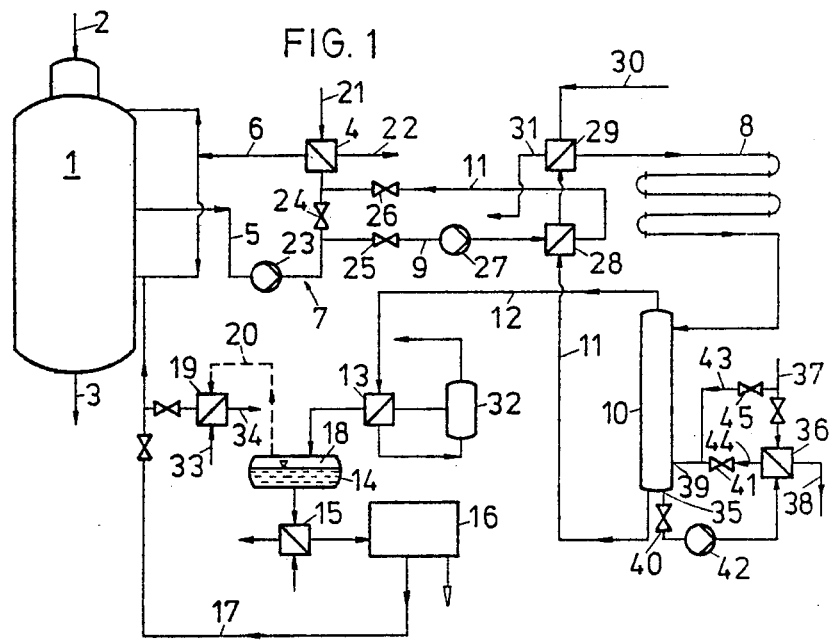

United States Patent [19]

Avignon et al.

[11] Patent Number: 4,916,242

[45] Date of Patent: Apr. 10, 1990

[54] COMBINED PROCESS FOR THERMALLY AND CHEMICALLY TREATING LIGNOCELLULOSE-CONTAINING BIOMASS AND FOR PRODUCING FURFURAL

[75] Inventors: Gerard Avignon, Agen, France; Wolfgang Jaeggle, Bodnegg, Fed. Rep. of Germany; Horst Steinmüller, Leonding; Karl Lackner, Linz, both of Austria

[73] Assignee: Voest-Alpine Industrieanlagenbau Gesellschaft m.b.H., Linz, Austria

[21] Appl. No.: 193,828

[22] Filed: May 12, 1988

[30] Foreign Application Priority Data

May 12, 1987 [AT] Austria ................................ 1189/87

[51] Int. Cl.⁴ .......................................... C07D 307/50
[52] U.S. Cl. .................... 549/489; 549/490; 162/14; 162/15; 162/16
[58] Field of Search .................. 549/489, 490; 167/14, 167/16, 15

[56] References Cited

U.S. PATENT DOCUMENTS

| | | |
|---|---|---|
| 2,859,108 | 11/1958 | Rosenblad ............................. 162/83 |
| 3,085,038 | 4/1963 | Rovesti ................................ 162/16 |
| 3,532,597 | 10/1970 | Ljungqvist ............................ 162/84 |
| 3,738,908 | 6/1973 | Villavicencio ........................ 162/84 |
| 4,070,232 | 1/1978 | Funk ..................................... 162/16 |
| 4,155,804 | 5/1979 | Edge, Jr. ............................... 162/16 |
| 4,366,322 | 12/1982 | Raymond ............................. 549/489 |
| 4,401,514 | 8/1988 | Kenzler et al. ....................... 203/15 |

FOREIGN PATENT DOCUMENTS 3435451 10/1986 Fed. Rep. of Germany .

*Primary Examiner*—Richard L. Raymond
*Attorney, Agent, or Firm*—Ostrolenk, Faber, Gerb & Soffen

[57] ABSTRACT

In a combined process for the thermal and chemical treatment of lignocellulose-containing biomass and for the production of furfural, biomass is supplied to a cooker in batches, is heated in the cooker under the addition of cooking liquor, and cellulose or pre-treated biomass is withdrawn from the cooker in batches. In order to guarantee a high yield of furfural, cooking liquor is withdrawn from the cooker during the heating phase and is fed to a furfural production plant, and the cooking liquor at least largely freed from pentoses and furfural is returned to the cooker.

7 Claims, 1 Drawing Sheet

COMBINED PROCESS FOR THERMALLY AND CHEMICALLY TREATING LIGNOCELLULOSE-CONTAINING BIOMASS AND FOR PRODUCING FURFURAL

The invention relates to a combined process for the thermal and chemical treatment of lignocellulose-containing biomass and for the production of furfural, wherein the biomass is supplied to a cooker in batches, is heated in the cooker under the addition of cooking liquor, and cellulose or pre-treated biomass is withdrawn from the cooker in batches, as well as to a plant for carrying out the process.

A process of this type is known, for instance, from DE-A - 34 35 451 and from EP-B 0 038 317. In DE-A - 34 35 451, a two-stage process comprising pre-hydrolysis and subsequent chemical hydrolysis is described for the production of celluloses and furfural. According to that process, the material to be hydrolyzed is heated in the presence of a diluted acid at temperatures of below 150° C. until the pentosans obtained have been hydrolyzed to pentoses. Thereafter, a hydrolyzing agent is fed and the temperature is rapidly raised to above 160° C. and maintained there until hydrolysis has been completed. The furfural forming from the pentoses is discharged.

In EP-B - 0 038 317, a process for the production of furfural and other organic compounds from acid hydrolysates of plants, in particular spent sulfite lyes, is described. There, the pentoses contained in the spent lyes are dehydrated to furfural by heating in a reactor to temperatures of up to 300° C.

The reaction course of the formation of furfural from pentosans contained in a lignocellulose-containing biomass comprises two reaction stages, which are favored by the addition of acids. The first stage consists in the absorption of water with the pentosans being converted into pentoses by hydrolysis and the second stage comprises dehydration to transform the pentoses into furfural With the process according to DE-A - 34 35 451, these two reaction stages take place during the chemical hydrolysis of the biomass. However, due to the drastic reaction conditions prevailing, this partially involves the formation of condensation products from furfural and decomposition reactions of the pentosans. The same disadvantages are found with the process according to EP-B - 0 038 317, in which furfural is formed from the spent lye only upon hydrolysis. Hence follows a strongly reduced furfural yield as compared to the maximum furfural yield theoretically possible, with these two processes on account of the formation of condensation products, which also will have adverse effects if bleached sulfite cellulose is produced.

The invention aims at avoiding these difficulties and disadvantages and has as its object to provide a combined process of the initially defined kind as well as a plant for carrying out this process, by which the formation of secondary products from pentoses in the cooking procedure itself is prevented so as to increase the yield of furfural and with which only a slight amount of bleaching agent is required for the production of bleached sulfite cellulose.

According to the invention, this object is achieved in that cooking liquor is withdrawn from the cooker during the heating phase, if desired even during the cooking phase, and is fed to a furfural production plant, and that the cooking liquor at least largely freed from pentoses and furfural is returned to the cooker, wherein the cooking liquor, during the cooking phase, primarily is conducted through a heat exchanger only.

The reaction conditions of the heating phase, which are mild as compared to the subsequent hydrolysis phase, in particular its low temperature, enable the hydrolysis of the pentosans to pentoses and, at the same time, prevent any further reaction into furfural and its condensation products. Thereby, the yield of pentoses and, thus, furfural is strongly increased in the first place, and, at the production of cellulose, the purity of the latter is improved, in the second place. Hence follows a reduced use of bleaching agent at further processing. Recycling of the cooking liquor enables the continuous separation of pentoses without having to interrupt the heating phase. Moreover, the depletion of cooking liquor in the cooker is avoided.

According to a preferred embodiment, the pentoses contained in the cooking liquor are dehydrated to furfural in the furfural production plant, the substrate obtained is subjected to a steam distillation, the remaining cooking liquor is returned into the cooker, and the condensed exhaust vapors are subjected to a single-or multi-stage distillation to separate the furfural.

It is also suitable, if the liquid occurring at the single- or multi-stage distillation is returned into the cooker.

Advantageously, the sulfur dioxide incurring at the steam distillation is returned into the cooker with the production of cellulose.

Thereby, the depletion of sulfur dioxide of the cooking liquor present in the cooker is avoided and the constant supplementation of the amount of sulfur dioxide that reaches the furfural production plant with the cooking liquor can be omitted.

Preferably, the pentose-containing cooking liquor is guided through the furfural production plant with an overall residence time ranging between 10 and 60 min, preferably between 10 and 25 min, the cooking liquor being heated to a temperature of between 130 ° and 180° C., preferably between 150 ° and 180° C., and being maintained in this range.

Naturally, the content of pentoses of the cooking liquor fluctuates during the heating phase. By determining an overall residence time in the furfural production plant at a predetermined temperature, it has become possible to adapt the dehydration reaction condition to the respective content of pentoses and, thus, to improve the furfural yield.

In order to adapt the reaction conditions to the raw material to be processed and to the mode of operation of the cooker in an optimum way, it may also be advantageous to remove the cooking liquor from the cooker subsequent to the heating phase of the following cooking phase.

A plant for carrying out the process according to the invention comprises a cooker, into which a feed duct for lignocellulose-containing biomass enters and to which there are connected a discharge duct for biomass thermally treated in the cooker as well as a branch duct leading to a heat exchanger, from which a return duct for the cooking liquor departs and runs into the cooker, and a furfural production plant including a pipe reactor, a reaction column and a consecutively arranged distillation means, which pipe reactor is connectable, via an entry duct, and which reaction column is connectable, via a return duct, with the cooker in a conveying manner.

According to a suitable embodiment, the distillation means is adapted to be connected with the cooker in a duct-like manner for recycling the liquid separated from furfural. Thus, the cooking liquor freed from furfural may be conveyed back into the cooker.

According to a further suitable embodiment, an exhaust vapors duct of the reaction column enters into a collecting basin connected with the distillation means, which collecting basin includes a gas space adapted to be connected with the cooker in a duct-like manner.

The process according to the invention and a plant for carrying out the process will be explained in more detail with reference to FIGS. 1 and 2 as well as by way of two exemplary embodiments. Both Figures represent block diagrams of the plant according to one embodiment each.

According to FIG. 1, a feed duct 2 enters into a cooker 1 to charge the cooker with cooking liquor and biomass. Furthermore, there are connected to the cooker 1 a discharge duct 3 for removing pre-treated biomass or sulfite cellulose as well as a branch duct 5 leading to a heat exchanger 4 provided to heat the cooking liquor. From the heat exchanger 4, a return duct 6 for the cooking liquor departs and runs into the cooker 1, thus closing a heating circuit 7. To the branch duct 5, there are connected in a by-pass like manner a pipe reactor 8 via an entry duct 9, and a reaction column 10 provided in series with the pipe reactor 8 via a return duct 11. From the reaction column, an exhaust vapors discharge duct 12 via a heat exchanger 13, a collecting basin 14 and a further heat exchanger 15, leads to a distillation means 16, which is connected with the cooker 1 via a duct 17 for distillation residue. If the above-described plant is used for the production of sulfite cellulose, the gas space 18 of the collecting basin 14 suitably may be connected to the cooker 1 via a heat exchanger 19 by means of a duct 20 illustrated in the Figures in broken lines.

The process according to the invention is performed in the following way:

As soon as the cooker 1 has been fed with lignocellulose-containing biomass and cooking liquor via feed duct 2, heating is initiated. To this end, cooking liquor is drawn off the cooker 1 via branch duct 5 and is conveyed into the heat exchanger 4, which is supplied with high-pressure steam (represented byarrows 21, 22), is heated there and is conveyed back into the cooker 1 via return duct 6. The circulation of the cooking liquor is effected by means of a pump 23 provided in the branch duct 5. Between the branching of the supply duct 9 and the entry of the return duct 11, a valve 24 is provided in the branch duct, which valve is opened at the direct circulation of the cooking liquor through the heat exchanger 4, whereas valves 25, 26, which are provided in the supply duct 9 and in the return duct 11, respectively, are closed.

As soon as pentosans have been hydrolyzed to pentoses and have been dissolved by the cooking liquor in the cooker, the valve 24 incorporated in the branch duct is closed and the valves 25 and 26 provided in the supply and return ducts are opened such that cooking liquor is continuously pumped into the pipe reactor 8 through supply duct 9 by the aid of a pump 27 arranged in the supply duct 9. In this manner, the cooking liquor is introduced into two heat exchangers 28 and 29 also provided in the supply duct and one (28) of which is supplied with cooking liquor returning via the return duct 11 and the other (29) of which is supplied with high-pressure steam (illustrated by arrows 30 and 31), and thereby is brought to the temperature necessary for the dehydration of pentoses to furfural. This reaction stage primarily takes place in the pipe reactor 8 and partially also in the reaction column 10, into which the cooking liquor is subsequently conducted. In the reaction column 10, the furfural formed is expelled from the cooking liquor by means of steam, i.e., is stripped, then is conducted into the heat exchanger 13 via the exhaust vapors discharge duct 12, is condensed there under the formation of secondary steam, and the aqueous furfural solution forming is collected in the collecting basin 14. The secondary steam forming in the heat exchanger 13 is condensed in a cooler 32 and is conveyed back to the heat exchanger 13.

The cooking liquor freed from furfural and drawn on the lower end of the reaction column 10 is continuously returned into the cooker by means of the return duct 11 via the heat exchangers 28 and 4 during the heating phase of the cooker 1.

Connection to the furfural production plant is maintained as long as the pentose concentration in the cooking liquor does not fall short of a determined limit value. Thereafter, thermal pre-treatment i effected by conducting the cooking liquor over the heating circuit 7 until the lignocellulose-containing biomass has been readily treated, whereupon the cooker is emptied and charged anew.

If the plant is operated for the production of sulfite cellulose, sulfur dioxide incurs in the gas space 18 of the collecting basin 14 and is heated in the heat exchanger 19, to which high-pressure steam is supplied as illustrated by arrows 33 and 34, and subsequently is returned into the cooker 1.

The aqueous furfural solution present in the collecting basin 14 is cooled in the heat exchanger 15 under the formation of secondary steam and is fed to the furfural distillation means 16, in which furfural is extracted in one or several stages. The distillation residue incurring is conveyed back into the cooker 1 via duct 17.

The supply of the reaction column 10 with heat suitably may be realized in two ways, both with the production of cellulose and with the preparation of pre-treated biomass.

According to FIG. 1, the cooking liquor is withdrawn from the reaction column on the lower end 35 thereof, is heated in the heat exchanger 36 by high-pressure steam (illustrated by arrows 37, 38) and is conveyed back into the reaction column 10 near its lower end 39. Circulation is controlled by means of valves 40 and 41 and a pump 42. From the high-pressure steam supply duct 37, a high-pressure steam branch duct 43 runs into the return duct 44 departing from the heat exchanger 36, a control valve 45 being provided in the high-pressure steam branch duct 43. By the interaction of the valves 40, 41 and 45, hot steam can be used both to supply heat to the heat exchanger 36 and to feed the reaction column 10.

Figure 2:
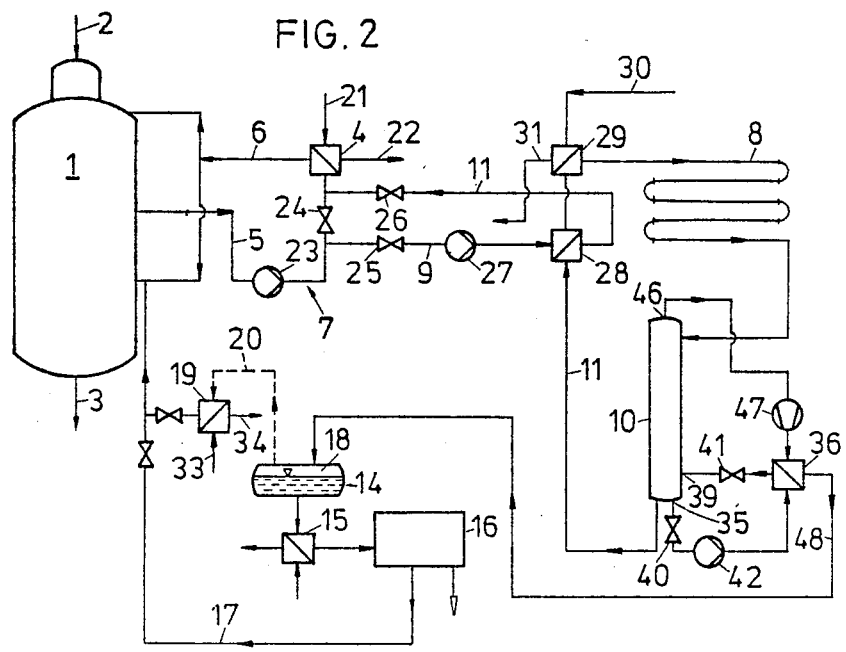

According to FIG. 2, the exhaust vapors leaving the reaction column 10 on its upper end 46 are compressed in a compressor 47 and are used to supply heat to the heat exchanger 36. The exhaust vapors condensed in the heat exchanger 36 subsequently are conducted into the collecting basin 14 via duct 48 and are processed as described above.

EXEMPLARY EMBODIMENT 1:

Cellulose is obtained from beech wood according to the magnesium bisulfite process by cooking in batches.
Raw material analysis of the beech wood:
Xylan:24.2%
Glucan:42.6%
Lignin:26.4%

36 tons of abs. dry beech wood are charged into the cooker 1, which has a capacity of 200 m$^3$. The hydraulic module is 1:3.5. The cooker 1 is heated by means of steam by cooking liquor circulation via the heating circuit 7 as described above. Upon reaching a temperature of approximately 120° C. within the cooker (after about 3 hours), about 60% of the pentoses has been set free, whereupon cooking liquor is branched off the heating circuit 7 of the cooker 1, is pre-heated by the cooking liquor already freed from pentoses by indirect heat exchange, and subsequently is further heated to a temperature of from 160° to 165° C.

The residence time within the pipe reactor 8 is controlled as a function of the pentose concentration via the flow rate. The overall residence time in the system pipe reactor 8—reaction column 10 amounts to 15 minutes. The exhaust vapors emerging from the reaction column 10, which is under pressure, contain the entire free $SO_2$ of the cooking lye and the furfural formed. These exhaust vapors are condensed by secondary steam forming simultaneously, the $SO_2$ contained therein is separated immediately and is conveyed back to the cooker 1 in the gaseous phase under pressure via duct 20 in order that the $SO_2$-content of the cooking lye remains constant. The distillation of furfural is effected in two stages.

If the content of the pentose concentration falls below 5 g/l, cooking liquor is conducted no longer through the furfural production plant, but through the heating circuit 7. The amount of furfural produced in this process from the charged material indicated amounts to 4,500 kg.

EXEMPLARY EMBODIMENT 2:

Furfural and pre-treated biomass are obtained from sugar millet bagasse by thermal treatment for subsequent enzymatic hydrolysis.

Upon reaching of a cooking temperature of about 150° C., pentose-containing cooking liquor is started to be continuously drawn off the cooker 1 with simultaneously returning the cooking liquor largely freed from pentoses from the furfural production plant. Since the reaction of pentoses to furfural is more efficient if carried out in a mineral-acid medium than by the acid catalysis of the organic acids from the raw material, approximately 0.5 to 2.0% sulfuric acid may be added to the cooking lye from the very beginning. The overall residence time in the system pipe reactor—reaction column amounts to 15 minutes.

With a pentose reaction degree in the pipe reactor of 8 to 80% and with a furfural yield of likewisely 80%, about 67 kg furfural per ton of sugar millet bagasse can be obtained in this way. The pre-treated biomass subsequently is heated to at least 200° C. in order to guarantee the maximum yield of glucose in a subsequent enzymatic hydrolysis.

What we claim is:

1. In a combined process for thermally and chemically treating lignocellulose-containing biomass and for producing furfural, by supplying lignocellulose-containing biomass and cooking liquor in the cooker in batches, heating said biomass and said cooking liquor in the cooker in a heating phase and cooking said biomass in a cooking phase subsequent to said heating phase enabling the formation of one of cellulose and pre-treated biomass, and withdrawing said one of cellulose and pre-treated biomass from the cooker in batches, the improvement comprising:
   heating said biomass and said cooking liquor in said heating phase in order to hydrolyze pentosans to pentoses;
   withdrawing cooking liquor from said cooker during said heating phase as soon as pentosans have been hydrolyzed to said pentose and have been dissolved in the cooking liquor, and supplying said cooking liquor with the pentoses dissolved therein to a furfural production plant;
   dehydrating the pentoses contained in said cooking liquor to furfural in the furfural production plant so as to obtain a liquid substrate containing furfural;
   subjecting said liquid substrate to steam distillation so as to obtain remaining cooking liquor and condensed exhaust vapors;
   returning said remaining cooking liquor into said cooker;
   subjecting said condensed exhaust vapors to an at least single-stage distillation to separate said furfural;
   withdrawing said one of cellulose and pretreated biomass from said cooking phase; and
   ceasing to supply said cooking liquor to said furfural production plant when the pentose concentration of said cooking liquor falls to below 5g/l.

2. A process as set forth in claim 1, comprising also withdrawing cooking liquor from the cooker during said cooking phase and supplying said cooking liquor removed during the cooking phase to said furfural production plant.

3. A process as set forth in claim 1, wherein a liquid incurs at said at least single-stage distillation, said liquid being returned into said cooker.

4. A process as set forth in claim 1, wherein $SO_2$ incurs during steam distillation with the production of cellulose, said $SO_2$ being returned into said cooker.

5. A process as set forth in claim 1, wherein said cooking liquor containing pentoses is guided through the furfural production plant with an overall residence time ranging between 10 and 60 minutes, said cooking liquor being heated to, and maintained at, a temperature of between 130° and 180° C.

6. A process as set forth in claim 5, wherein said residence time ranges between 10 and 25 minutes.

7. A process as set forth in claim 5, wherein said cooking liquor is heated to, and maintained at, a temperature of between 150 and 180° C.

* * * * *